US012611490B2

(12) United States Patent
Takahashi et al.

(10) Patent No.: US 12,611,490 B2
(45) Date of Patent: *Apr. 28, 2026

(54) POLYTETRAFLUOROETHYLENE TUBE AND MEDICAL TUBE USING SAME

(71) Applicant: Junkosha Inc., Kasama (JP)

(72) Inventors: Masamichi Takahashi, Kasama (JP);
Ayumi Matsuda, Kasama (JP);
Koichiro Yoshioka, Kasama (JP)

(73) Assignee: JUNKOSHA, INC., Kasama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/657,881

(22) Filed: May 8, 2024

(65) Prior Publication Data

US 2024/0285833 A1      Aug. 29, 2024

Related U.S. Application Data

(63) Continuation of application No. 18/222,174, filed on Jul. 14, 2023, now Pat. No. 11,998,663, which is a
(Continued)

(30) Foreign Application Priority Data

May 17, 2022   (JP) ................................. 2022-081112
Jan. 18, 2023   (JP) ................................. 2023-006194
(Continued)

(51) Int. Cl.
*A61L 29/06*      (2006.01)
*A61L 29/04*      (2006.01)
(52) U.S. Cl.
CPC ............. *A61L 29/06* (2013.01); *A61L 29/041* (2013.01)

(58) Field of Classification Search
None
See application file for complete search history.

(56) References Cited

U.S. PATENT DOCUMENTS 10,744,231 B1      8/2020   Wahab et al.
11,998,663 B2 *    6/2024   Takahashi ............... A61L 29/14
(Continued)

FOREIGN PATENT DOCUMENTS

EP            3412712 B1      10/2020
JP         2000316977 A      11/2000
(Continued)

OTHER PUBLICATIONS

Extended European Search Report Issued on Jul. 23, 2024 In Corresponding European Patent Application No. 23736589.5.
Anonymous: "Surface treatment of PTFE—Wikipedia", May 11, 2022 (May 11, 2022), XP093184689, Retrieved from the Internet: URL:https://en.wikipedia.org/w/index.php? title=Surface treatment of PTFE&oldid=1087284107.

*Primary Examiner* — Tae H Yoon
(74) *Attorney, Agent, or Firm* — Duane Morris LLP

(57)            ABSTRACT

The present invention provides a thin-walled PTFE tube with appropriate elongation, sufficient strength, and good uniformity during stretching and a medical tube with excellent flexibility and dimensional accuracy. The polytetrafluoroethylene tube according to the present invention is a polytetrafluoroethylene tube having a wall thickness of about 0.04 mm or less, wherein the wetting tension of either of or both outer and inner surfaces of the polytetrafluoroethylene tube is 46 mN/m or more, and in a stress-strain curve obtained by a tensile test performed under an atmosphere of 200° C., tensile stress at 20% strain $\sigma_{20}$ (N/mm²) of the polytetrafluoroethylene tube and tensile stress at 50% strain $\sigma_{50}$ (N/mm²) of the polytetrafluoroethylene tube satisfy $2.0 \leq 0.1 \times \sigma_{20} + 0.3 \times \sigma_{50} < 5.5$ (Inequality (1)).

6 Claims, 2 Drawing Sheets

Related U.S. Application Data continuation of application No. PCT/JP2023/018302, filed on May 16, 2023.

(30)        Foreign Application Priority Data

| | | |
|---|---|---|
| Mar. 6, 2023 | (JP) | ................................. 2023-033704 |
| May 14, 2023 | (JP) | ................................. 2023-079744 |

(56)            References Cited

U.S. PATENT DOCUMENTS

| | | |
|---|---|---|
| 2004/0213936 A1 | 10/2004 | Yoshimoto et al. |
| 2009/0234329 A1 | 9/2009 | Inamoto et al. |
| 2011/0180955 A1 | 7/2011 | Inamoto et al. |

FOREIGN PATENT DOCUMENTS

| | | | |
|---|---|---|---|
| JP | 2004340364 | A | 12/2004 |
| JP | 2008086470 | A | 4/2008 |
| JP | 2013176583 | A | 9/2013 |
| JP | 6244490 | B1 * | 12/2017 |
| JP | 2018038783 | A | 3/2018 |
| JP | 2019130880 | A | 8/2019 |
| WO | WO 2015/009548 | A1 * | 1/2015 |
| WO | 2021025814 | A1 | 2/2021 |
| WO | 2021/126904 | | 6/2021 |

* cited by examiner

【FIG. 1】
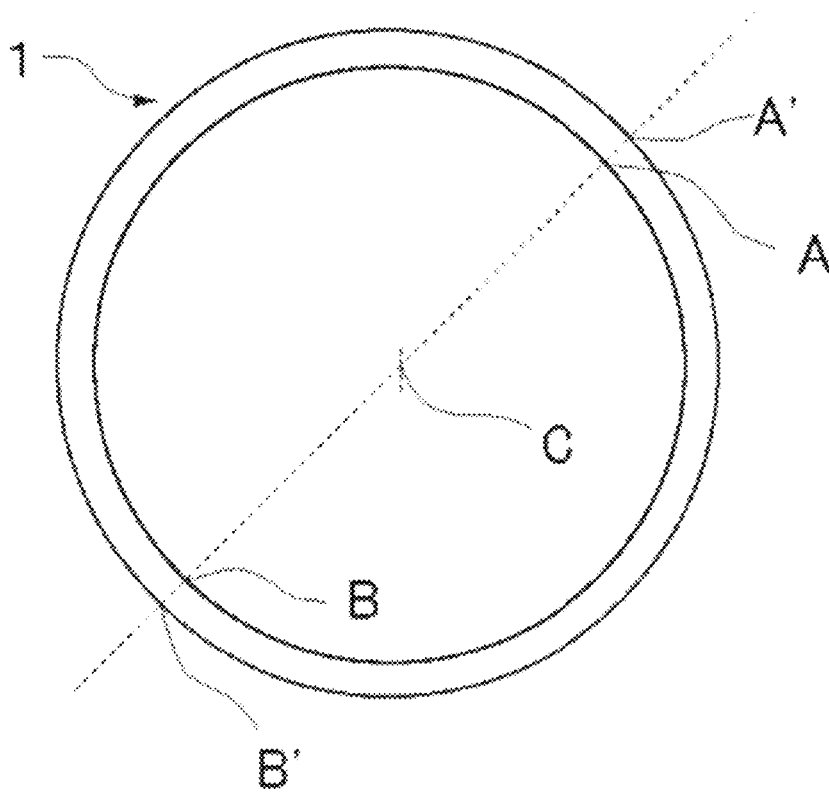

【FIG. 2】
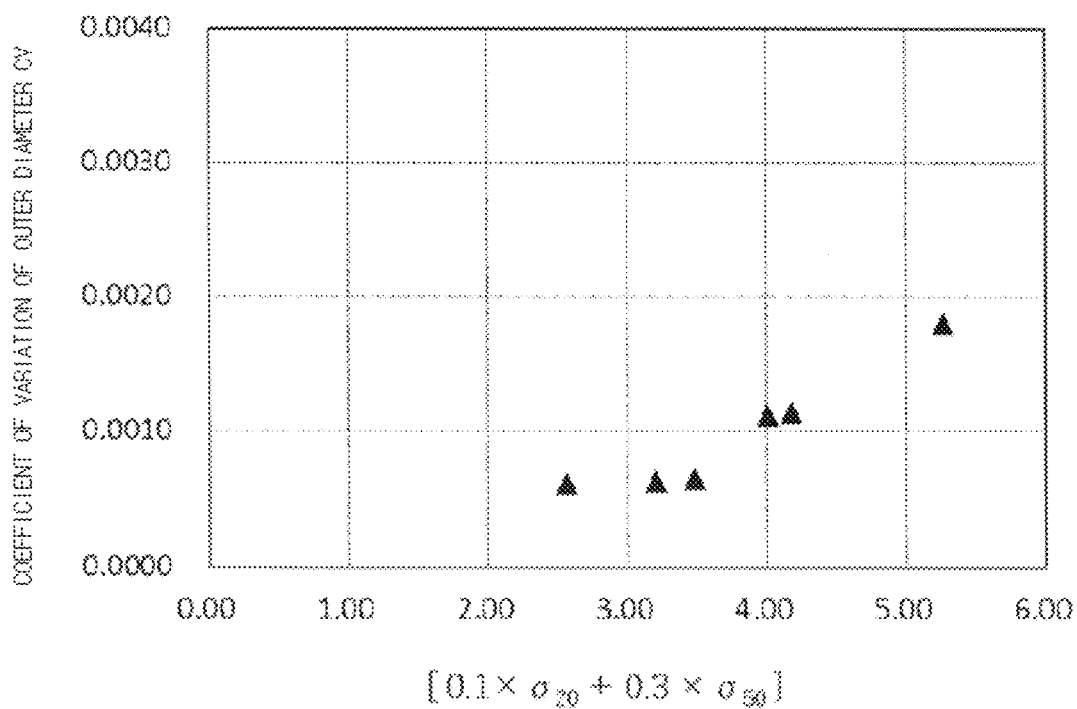

POLYTETRAFLUOROETHYLENE TUBE AND MEDICAL TUBE USING SAME

CROSS-REFERENCE TO RELATED APPLICATIONS

This application is a continuation of U.S. Application Ser. No. 18/222,174 filed Jul. 14, 2023, now U.S. Pat. No. 11,998,663 issued Jun. 4, 2024, which is a Bypass Continuation application of International Application No. PCT/JP2023/018302 filed May 16, 2023, and claims priority to Japanese Patent Application Nos. 2022-081112 filed May 17, 2022; 2023-006194 filed Jan. 18, 2023; 2023-033704 filed Mar. 6, 2023; and 2023-079744 filed May 14, 2023, the disclosures of which are hereby incorporated by reference in their entireties.

BACKGROUND OF THE INVENTION

Field of the Invention

The present invention relates to a fluoropolymer tube, and more particularly to a thin-walled tube made of polytetrafluoroethylene (hereinafter referred to as "PTFE").

Description of Related Art

Endovascular surgery, in which a catheter is inserted into a blood vessel to remove or treat a lesion in the blood vessel, is becoming a mainstream procedure because burden on the patient is less. A catheter used for such an application is percutaneously inserted into the body, and it is necessary for the tip of a tube to reach a lesion via the blood vessel. Therefore, the catheter is required to have straightness to move straight through the blood vessel and operability to transmit the operation of a surgeon who performs the treatment. In order to satisfy these requirements, the catheter is configured by stacking layers having different characteristics. Since the inside of the catheter needs to correspond to operations, such as insertion of a treatment jig and injection of a medicinal fluid, the inner surface of the catheter is required to have low friction and high strength, and the inner diameter of the catheter is required to be as large as possible. On the other hand, it is necessary for the outer diameter of the catheter to be small in consideration of the burden on a patient. Therefore, it is preferable for each layer of the catheter to be as thin as possible.

A PTFE tube is appropriately used in medical and other applications due to excellent properties thereof, such as chemical resistance, non-adhesiveness, and low friction. There is a method of coating a core wire with PTFE, forming an outer resin layer thereon, and pulling out the core wire to obtain a catheter tube as one method of manufacturing the catheter tube. There is a method of applying a PTFE dispersion liquid to a core wire and sintering the same (hereinafter referred to as a "dipping method") and a method of directly extruding a paste onto the core wire to cover the core wire with the paste as methods of coating the core wire with PTFE.

In addition, there is a method of covering the core wire with a PTFE tube molded so as to have a thin wall. In this method, the core wire is inserted into the PTFE tube, and the PTFE tube is stretched in this state such that the diameter thereof is reduced, whereby the PTFE tube comes into contact with the surface of the core wire. In this method, it is necessary for the PTFE tube that is used to have both the strength to withstand stretching and the elongation to allow stretching. Also, in a catheter manufacturing process, which requires high dimensional accuracy, it is necessary for the PTFE layer on the core wire to have a uniform wall thickness, and it is necessary for the PTFE tube that is stretched to have high dimensional accuracy and uniform elongation.

PTFE has a very large melt viscosity, and a long PTFE molded product is generally formed by paste extrusion molding rather than melt extrusion molding. However, it is difficult to mold a thin-walled tube by paste extrusion. In order to mold a thin-walled PTFE tube, therefore, a dipping method of applying a PTFE dispersion liquid applied to a core wire, sintering the same, and removing the core wire to obtain a tube is frequently used (see, for example, Patent Document 1). However, a tube molded by the dipping method is subject to defects, such as pinholes, and has inferior strength. In addition, Patent Document 2 discloses a method of forming a PTFE resin on a metal core wire by paste extrusion molding to obtain a thin-walled tube. Paste extrusion promotes flow orientation of PTFE particles and improves the tensile strength of the tube; however, the strength of the tube is not sufficient to improve performance of the catheter.

Patent Document 3 discloses a method of molding a PTFE tube by paste extrusion molding and stretching the PTFE tube in a longitudinal direction to thin the tube. Stretching the PTFE tube results in thinning of the tube and securing of strength of the tube, but elongation and flexibility of the tube are lost.

PRIOR ART DOCUMENTS

Patent Documents

Patent Document 1: Japanese Patent Application Publication No. 2000-316977
Patent Document 2: Japanese Patent Application Publication No. 2013-176583
Patent Document 3: Japanese Patent Application Publication No. 2004-340364

SUMMARY OF THE INVENTION

Technical Problem

The present invention has been made in view of the above problems of a conventional thin-walled PTFE tube, and it is an object of the present invention to provide a thin-walled PTFE tube with appropriate elongation, sufficient strength, and good uniformity during stretching, which is necessary when the PTFE tube is used to coat a core wire, etc., and a medical tube with excellent flexibility and dimensional accuracy.

Technical Solution

In order to accomplish the above object, the configuration described in the claims may be employed. For example, the present invention provides a polytetrafluoroethylene tube having a wall thickness of about 0.04 mm or less, wherein the wetting tension of either of or both outer and inner surfaces of the polytetrafluoroethylene tube is 46 mN/m or more, and in a stress-strain curve obtained by a tensile test performed under an atmosphere of 200° C., tensile stress at 20% strain $\sigma_{20}$ (N/mm$^2$) of the polytetrafluoroethylene tube and tensile stress at 50% strain $\sigma_{50}$ (N/mm$^2$) of the polytetrafluoroethylene tube satisfy $2.0 \leq 0.1 \times \sigma_{20} + 0.3 \times \sigma_{50} < 5.5$ (Expression (1)).

In a preferred embodiment, the polytetrafluoroethylene tube has a tensile strain at break of 200% or more in the tensile test performed under an atmosphere of 200° C., and the tensile stress at 20% strain $\sigma_{20}$ of the polytetrafluoroethylene tube in the tensile test performed under an atmosphere of 200° C. is 4.0 (N/mm$^2$) or more.

In addition, the following configuration as described in the claims may be employed. For example, the present invention provides a polytetrafluoroethylene tube having a wall thickness of about 0.04 mm or less, wherein the inner diameter of the polytetrafluoroethylene tube is about 3.0 mm or less, and in a stress-strain curve obtained by a tensile test performed under an atmosphere of 200° C., tensile stress at 20% strain $\sigma_{20}$ (N/mm$^2$) of the polytetrafluoroethylene tube and tensile stress at 50% strain $\sigma_{50}$ (N/mm$^2$) of the polytetrafluoroethylene tube satisfy $2.0 \leq 0.1 \times \sigma_{20} + 0.3 \times \sigma_{50} < 5.5$ (Inequality (1)).

Also, in another example, the present invention provides a medical tube using a polytetrafluoroethylene tube, wherein the polytetrafluoroethylene tube has a wall thickness of about 0.04 mm or less, the wetting tension of either of or both outer and inner surfaces of the polytetrafluoroethylene tube is 46 mN/m or more, and in a stress-strain curve obtained by a tensile test performed under an atmosphere of 200° C., tensile stress at 20% strain $\sigma_{20}$ (N/mm$^2$) of the polytetrafluoroethylene tube and tensile stress at 50% strain $\sigma_{50}$ (N/mm$^2$) of the polytetrafluoroethylene tube satisfy Inequality (1) above.

In addition, the present invention provides a medical tube using a polytetrafluoroethylene tube, wherein the polytetrafluoroethylene tube has a wall thickness of about 0.04 mm or less, the inner diameter of the polytetrafluoroethylene tube is about 3.0 mm or less, and in a stress-strain curve obtained by a tensile test performed under an atmosphere of 200° C., tensile stress at 20% strain $\sigma_{20}$ (N/mm$^2$) of the polytetrafluoroethylene tube and tensile stress at 50% strain $\sigma_{50}$ (N/mm$^2$) of the polytetrafluoroethylene tube satisfy Inequality (1) above.

Furthermore, in another example, the present invention provides a medical tube including a polytetrafluoroethylene liner prepared by processing a polytetrafluoroethylene tube, the polytetrafluoroethylene liner having a wall thickness of about 0.04 mm or less, wherein an inner diameter of the polytetrafluoroethylene liner is about 3.0 mm or less, and in a stress-strain curve obtained by a tensile test performed under an atmosphere of 200° C., tensile stress at 20% strain $\sigma'_{20}$ (N/mm$^2$) of the polytetrafluoroethylene liner and tensile stress at 50% strain $\sigma'_{50}$ (N/mm$^2$) of the polytetrafluoroethylene liner satisfy $2.4 \leq 0.1 \times \sigma'_{20} + 0.3 \times \sigma'_{50} < 6.6$ (Inequality (2)).

Advantageous Effects

A PTFE tube according to the present invention has strength, appropriate elongation, and good uniformity when stretched, and therefore the PTFE tube is suitable for use in applications where the PTFE tube is stretched. The PTFE tube provided on a core wire by coating is uniform, has small dimensional variation, and has excellent flexibility and dimensional accuracy. The PTFE tube according to the present invention is capable of being used in products requiring high dimensional accuracy and is particularly suitable as a liner for medical tubes.

BRIEF DESCRIPTION OF THE DRAWINGS

FIG. 1 is a schematic sectional view illustrating the dimensions of a PTFE tube according to the present invention.

FIG. 2 is a view showing a relationship between the middle portion of Inequality (1) related to the PTFE tube according to the present invention and variation in outer diameter thereof (coefficient of variation CV).

DESCRIPTION OF THE INVENTION

Hereinafter, a PTFE tube according to an embodiment of the present invention will be described in detail. The embodiment described below is not intended to limit the invention defined in the claims, and not all combinations of features described in the embodiment are essential to implementation of the present invention.

In the embodiment of the present invention, the wall thickness of the PTFE tube is about 0.04 mm or less. Specifically, the wall thickness of the PTFE tube is about 0.005 mm to about 0.04 mm, preferably about 0.01 mm to about 0.04 mm, more preferably about 0.01 mm to about 0.03 mm. The thin wall thickness contributes to decrease in diameter of a catheter without interfering with the function of the catheter when used as a part of a catheter layer. At least, it is preferable for the wall thickness to be sufficient to secure airtightness of the tube. The wall thickness of the PTFE tube may be confirmed by measuring the cross section of PTFE tube cut perpendicularly to a longitudinal axis direction using a microscope or the like. Alternatively, if it is possible to measure the inner diameter of the PTFE tube using a pin gauge, the inner diameter may be measured using the pin gauge, and the outer diameter can be measured using a dial gauge or the like in the state in which the pin gauge is inserted into an end of the tube, whereby the wall thickness of the PTFE tube may be calculated by the formula (wall thickness=(outer diameter−inner diameter)/2). Also, in the embodiment of the present invention, the inner diameter of the PTFE tube is about 3.0 mm or less. Specifically, the inner diameter of the PTFE tube is preferably about 0.20 mm to about 3.0 mm, more preferably about 0.25 mm to about 2.0 mm. FIG. 1 is a schematic view of the cross section 1 of the PTFE tube, illustrating the dimensions of the tube. When the cross section of the tube is circular, the inner diameter of the tube means the inner diameter of the cross section of the tube. Referring to FIG. 1, the inner diameter is the diameter of an inner circle, and is the linear distance between points A and B on the inner circle on a straight line passing through the center C of the inner circle. The inner diameter is evenly measured at 2 points (2 points at which the angle of the straight line is changed by about 90°) to 4 points (4 points at which the angle of the straight line is changed by about 45°), and the average value thereof is adopted as the inner diameter of the PTFE tube. The wall thickness of the PTFE tube is the distance between point A on the inner circle and point A' on an outer circle on the straight line passing through the center C of the circle. In addition, the wall thickness of the PTFE tube is the distance between point B on the inner circle and point B' on the outer circle. The wall thickness is evenly measured at about 4 to 8 points, and the average value thereof is adopted as the wall thickness of the PTFE tube.

In a stress-strain curve obtained by a tensile test performed under an atmosphere of 200° C., on the assumption that the tensile stress of the polytetrafluoroethylene tube at 20% elongation (tensile stress at 20% strain) is $\sigma_{20}$ (N/mm$^2$) and the tensile stress of the polytetrafluoroethylene tube at 50% elongation (tensile stress at 50% strain) is $\sigma_{50}$ (N/mm$^2$), the PTFE tube according to the present invention is capable of solving the problem of the present invention if Inequality (1) is satisfied (when the wall thickness thereof is 0.04 mm or less). Inequality (1) was obtained from the result of data analysis, and has a high correlation with uniformity of PTFE tube during stretching.

$$2.0 \le 0.1 \times \sigma_{20} + 0.3 \times \sigma_{50} < 5.5 \qquad \text{Inequality (1)}$$

The value of the right side of Inequality (1) is preferably 5.5, more preferably 5.0. If the value of the left side of Inequality (1) is too small, the PTFE tube may not be strong enough when stretched. The value of the left side of Inequality (1) is preferably 2.0, more preferably 3.0. In addition, the PTFE tube according to the present invention tends to be more effective if Inequality (1) is satisfied when the inner diameter thereof is about 3.0 mm or less.

When an outer resin layer or the like is formed on the PTFE tube, both the value of the right side and the value of the left side of Inequality (1) for a PTFE liner obtained by processing the PTFE tube tend to increase by about 20%. Consequently, the value obtained by subtracting about 20% from the above value obtained for the PTFE liner may be treated as the value of the PTFE tube according to the present invention.

In addition, it is preferable for the polytetrafluoroethylene tube according to the present invention to have a tensile strain at break of 200% or more in a tensile test performed under an atmosphere of 200° C. In addition, it is preferable for the tensile stress at 20% strain $\sigma_{20}$ of the polytetrafluoroethylene tube in a tensile test performed under an atmosphere of 200° C. to be 4.0 (N/mm$^2$) or more. In addition, it is preferable for the tensile stress at 20% strain $\sigma_{20}$ of the polytetrafluoroethylene tube to be less than 11.0 (N/mm$^2$).

In addition, it is preferable for the tensile stress at 50% strain $\sigma_{50}$ of the polytetrafluoroethylene tube according to the present invention to be equal to or greater than 6.0 (N/mm$^2$) in a tensile test performed under an atmosphere of 200° C. In addition, it is preferable for the tensile stress at 50% strain $\sigma_{50}$ of the polytetrafluoroethylene tube to be less than 14.0 (N/mm$^2$).

A medical tube using the PTFE tube according to the present invention having strength and appropriate elongation may be made into a tube having good flexibility.

The PTFE tube according to the present invention has a wetting tension of 46 mN/m or more, preferably 60 mN/m or more, on either of or both the outer and inner surfaces of the tube. The wetting tension on the surface of the PTFE tube may be adjusted by etching (physically or chemically modifying) the surface. Specifically, etching may be performed using plasma, corona discharge, or ion beams, or a mixture of metal sodium and ammonia or naphthalene. For example, in etching using a naphthalene+metal sodium+diglyme solution, it is also possible to achieve a wetting tension of 70 mN/m or more on the surface of the tube. The PTFE tube according to the present invention has a wetting tension of 46 mN/m or more on the outer surface of the tube, and especially when used as a liner for a medical tube, the strength of the inner layer (PTFE layer) may be easily maintained against a load applied to an inner surface of the medical tube.

Hereinafter, the embodiment of the present invention will be described in detail.

There are two types of PTFE powder used in molding of a tube: fine powder and molding powder. Fine powder, which has a property of being deformed with fibrillation when shear stress is applied, is preferred for use in the embodiment of the present invention. A polytetrafluoroethylene resin used in embodiments of the present invention may be a homopolymer of tetrafluoroethylene (hereinafter referred to as "TFE") or modified PTFE. Modified PTFE is formed by polymerization of TFE and a small amount of a monomer other than TFE. The monomer other than TFE includes, for example, chlorotrifluoroethylene (CTFE), hexafluoropropylene (HFP), and perfluoroalkyl vinyl ether (PAVE). In general, modified PTFE is used to improve properties, such as heat resistance, abrasion resistance, and flexural resistance, of a molded product. The polytetrafluoroethylene resin used in the embodiment of the invention may be a single PTFE species listed above or a blend of multiple species. In addition, the polytetrafluoroethylene tube according to the present invention may include a polymer other than the polytetrafluoroethylene resins described above in a small amount as long as the function thereof is not impaired.

PTFE fine powder is generally composed of primary particles having an average particle diameter of 0.2 to 0.5 μm that aggregate to form secondary particles having an average particle diameter of 400 to 700 μm. Even at room temperature, the PTFE fine powder easily fibrillates and forms a clump when vibrated. This property is used in paste extrusion molding. In general, paste extrusion molding is a method in which PTFE is mixed with an organic solvent called an auxiliary agent (lubricant) and compressed to prepare a preform, and the preform is introduced into an extruder that applies pressure to extrude the preform into a film, a tube, a wire coating material, or the like. Since uniformity of the extrusion-molded PTFE tube is important in the PTFE tube according to the present invention, it is preferable to prepare the PTFE preform such that the internal structure of the preform is uniform. Specifically, for example, the PTFE fine powder mixed with the auxiliary agent before creating the preform is handled so as not to form lumps, and it is preferable for any lump formed to be removed using a sieve before introducing the preform into a compression die.

The auxiliary agent is added to the PTFE fine powder to form a paste that can be formed by an extruder. It is preferable for the auxiliary agent used in the embodiment of the present invention to be an organic solvent having high lubricity. After the auxiliary agent is added to the PTFE fine powder, the PTFE fine powder and the auxiliary agent are molded into a tube through the die by the extruder; however, if the auxiliary agent volatilizes during molding, stable molding is difficult, which is undesirable. It is preferable for the auxiliary agent used in the embodiment of the present auxiliary agent used in the embodiment of the present invention to have an initial boiling point (IBP) of 150° C. or higher. After the PTFE fine powder and the auxiliary agent are molded into a tube shape, the auxiliary agent is volatilized and removed before the tube is sintered. At this time, it is preferable for the IBP of the auxiliary agent to be 250° C. or less in order to definitely remove the auxiliary agent. A petroleum-based solvent or the like is frequently used as an organic solvent having high lubricity and an IBP of 150° C. to 250° C.

It is more preferable for the auxiliary agent used in the embodiment of the present invention to have an interfacial tension of 3 mN/m or higher than the interfacial tension of PTFE, which is 18.5 mN/m. Since the interfacial tension of the auxiliary agent is high, it is thought that the auxiliary agent easily stays on surfaces of the PTFE particles without moving between the particles more than necessary. In paste extrusion molding of PTFE, the PTFE particles slide against each other in the die during extrusion, and the surfaces of the particles become fibrillated. When the fibrils become entangled, the fibrils become less fluid, and extrusion pressure increases. At this time, the auxiliary agent present around the PTFE particles enhances lubricity between the PTFE particles and between the PTFE particles and an inner wall of the die, thereby appropriately inhibiting entanglement between the PTFE particles and preventing an excessive increase in extrusion pressure. For example, when a PTFE tube having a wall thickness of 0.04 mm or less is extrusion-molded, a flow path in the die is extremely narrow and the resin flows under high reduction ratio (hereinafter referred to as "RR") conditions, whereby shear force between the inner wall of the die and the PTFE particles and between the PTFE particles increases. When high shear stress is suddenly applied to the PTFE particles, the PTFE particles fibrillate at once and the extrusion pressure increases. However, the auxiliary agent that stays between the PTFE particles reduces the shear force between the PTFE particles and between the PTFE particles and the inner wall of the die, thereby inhibiting too rapid fibrillation of PTFE.

The tube according to the embodiment of the present invention may be made of polytetrafluoroethylene resin containing a filler or another resin. Examples of the filler may include carbon, a metal oxide such as alumina, sintered PTFE, a resin filler made of a fluoropolymer other than PTFE or another resin. One or more of the above fillers may be mixed with PTFE. Also, it is possible to configure a PTFE tube so as to have a plurality of layers and to dispose a layer containing a filler or another resin only in any one of the layers.

Hereinafter, a method of manufacturing the tube according to the embodiment of the present invention will be described.

Molding of Preform

PTFE fine powder and an auxiliary agent are mixed with each other using a tumbler, etc. When a filler, etc. is added to PTFE, the same may be added in this process. PTFE fine powder is used after removing lumps therefrom using a sieve, etc. After the mixture of the PTFE and the auxiliary agent is passed through a sieve to remove the lumps therefrom, the mixture is compressed and pressure-molded to prepare a preform. It is preferable for the preform to be uniformly compressed throughout the interior thereof. When a PTFE tube is configured so as to have a plurality of layers, for example, preforms having different sizes are combined to prepare a preform configured so as to have a plurality of layers.

Extrusion Molding

The prepared preform is set in an extruder and is molded into a tube shape through a die.

The outlet temperature of the die of the extruder is preferably 80° C. to 150° C., more preferably 90° C. to 120° C. When the temperature of the die is high, fibrillation on surfaces of PTFE particles is promoted, whereby entanglement of the molded fibrils tends to be strong. In addition, the cooling rate of the tube extruded from the die may also affect the value of the tensile stress at 20% strain $\sigma_{20}$ and the value of the tensile stress at 50% strain $\sigma_{50}$ of the polytetrafluoroethylene tube. For example, when the periphery of the die is covered by a heater after PTFE is discharged from the outlet of the die, it is possible to adjust the temperature of PTFE in a tube shape around the outlet of the die. In the PTFE tube according to the present invention, a temperature of 60° C. to 120° C. is considered appropriate. It is preferable to uniformly adjust the extrusion speed and extrusion temperature of the preform and to perform molding in the state in which the extrusion pressure is uniform. It is good for extrusion of the tube to be performed under constant and stable conditions, and it is good for the balance between supply and withdrawal (winding) of the tube to be adjusted in order to handle the molded tube such that the tube is not overloaded from the tube extrusion molding process to a drying process and a tube sintering process.

Drying Process

PTFE molded into the tube shape is heated while passing through a heating furnace set at a temperature equal to or lower than the melting point of PTFE to volatilize the auxiliary agent. When PTFE is sintered in a subsequent process, the auxiliary agent is sufficiently volatilized because the state in which a large amount of the auxiliary agent remains is undesirable for quality of the tube. When the IBP of the auxiliary agent is 150° C. to 250° C., it is possible to easily and sufficiently remove the auxiliary agent in the drying process. It is preferable to adjust the line tension by adjusting balance between supply and withdrawal of the tube in order to inhibit the tube from being stretched during the drying process.

Tube Sintering Process

Dried PTFE molded into the tube shape is heated to a temperature equal to or higher than the melting point of PTFE so as to be sintered. Normally, the sintering temperature is about 400° C. When PTFE constituting the tube is heated to a temperature equal to or higher than the melting point, PTFE particles are fused to each other to form a PTFE tube.

Etching Process

The surface of the PTFE tube is physically and/or chemically etched.

The present invention will be described in more detail with reference to the following examples. The following examples are intended to illustrate the invention and are not intended to limit the content of the present invention.

EXAMPLES

<Tensile Test Performed Under Atmosphere of 200° C.>

A tensile test was performed under the following test conditions under an atmosphere of 200° C. using a testing machine capable of performing a tensile test while controlling the sample temperature in a thermostatic bath.

Tensile Test Conditions

Test temperature 200° C.±3° C.

Initial distance between chucks 50 mm

Test speed 50 mm/min

A tube cut to a length suitable for measurement was used as a measurement sample without change, and measurement was continued until the tube broke to obtain data. The number of test samples was set to as 5 or more as possible, and the arithmetic mean of measured values was used for each stress value. Tensile strain $\varepsilon$ (%), which is a value obtained by dividing an increase in distance between chucks $\Delta L$ (mm) by an initial distance between chucks $L_0$ (mm), was calculated as $\varepsilon$ (%)=($\Delta L/L_0$)×100. The stress when the tube set in the chucks of the testing machine was elongated by 20% in a longitudinal direction (10 mm elongation) was defined as tensile stress at 20% strain $\sigma_{20}$ or $\sigma'_{20}$, and the stress when the tube was elongated by 50% in the longitudinal direction (25 mm elongation) was defined as tensile stress at 50% strain $\sigma_{50}$ or $\sigma'_{50}$. When a liner of a tube including a PTFE tube as the liner and an outer resin layer formed on the liner is measured, the outer resin layer may be peeled off and removed with a dissolving agent, etc. and the tensile test may be performed on only the liner.

<Heat Stretching Test>

A core wire having a length about 20 mm shorter than each tube was inserted into tube samples cut to a length of 1000 mm or more (20 samples were prepared.). At one end, ends of the tube and the core wire were aligned with each other and were fixed to a laminator. At the other end, a weight was fixed to only the tube so as to be suspended therefrom. Here, the weight of the weight was 150 g per 0.1 mm² of the sectional area of the tube. A heater heated to 300° C. heated the suspended tube while moving from top to bottom of the tube to stretch the PTFE tube and to laminate the same on the core wire. The moving speed of the heater was 100 mm/min. The core wire laminated with the PTFE tube (hereinafter referred to as a "coated core wire") was cooled and the dimensions thereof were measured. Since a core wire with a constant outer diameter is used, it is possible to calculate the wall thickness of a coated PTFE tube from the outer diameter of the coated core wire and the outer diameter of the core wire. Here, the variation in the outer diameter of the coated core wire was treated and evaluated as the variation in elongation of the coated PTFE tube. The dimensions of the coated core wire were measured at the portions excluding tens of millimeters from both ends of the coated core wire, because the tens of millimeters of the ends may be damaged during a lamination process. The outer diameter was measured at six or more points as evenly as possible over the entire length of one coated core wire. Measurement was performed evenly in a radial direction (sectional direction) at about 2 points (2 points at which the measurement angle is changed by 90°) to about 4 points (4 points at which the measurement angle is changed by 45°) per measurement point, and the arithmetic mean of measured values was taken as the outer diameter $D_0$ of the measurement point. In addition, measurement was performed as described above at six or more points over the entire length in one sample, and the arithmetic mean of the outer diameter $D_0$ at each measurement point was taken as the average outer diameter D of the sample. In addition, the variation of the outer diameter in the sample was checked by calculating a coefficient of variation of the outer diameter in the sample. The coefficient of variation $CV_D$ of the outer diameter in one sample was calculated by calculating the deviation of the outer diameter (the outer diameter $D_0$ of the measurement point–the mean outer diameter D) and the variance of the outer diameter (the mean square of the deviation of the outer diameter), calculating the standard deviation of the outer diameter (the square root of the variance of the outer diameter), and dividing the standard deviation of the outer diameter by the mean outer diameter D. The same process was performed for the remaining 19 samples. The arithmetic mean of the calculated coefficients of variation $CV_D$ of the outer diameter in the 20 samples was taken as the "coefficient of variation CV of the outer diameter".

<Wetting Tension Test>

Wetting tension was measured in accordance with ISO 8296. Specifically, a test mixture liquid for wetting tension measurement (a wetting tension test mixture liquid) was quickly applied to the surface of the PTFE tube using a cotton swab, and the state of a liquid film thereof was determined. If there is no change in the state of a line drawn by the cotton swab for 2 seconds, it is determined that the surface tension of the PTFE tube is equal to or greater than the surface tension of the wetting tension test mixture liquid. Conversely, if the width of the line of the wetting tension test mixture liquid drawn by the cotton swab is reduced in less than 2 seconds or if the liquid film breaks, a mixture liquid having lower surface tension than the wetting tension test mixture liquid is used for evaluation.

Example 1

100 parts by mass of PTFE fine powder, from which lumps were removed by a sieve, and 18 parts by mass of an auxiliary agent were introduced into a container and were mixed with each other, lumps were removed by the sieve, and the mixture was compressed to prepare a preform. The preform was introduced into an extrusion molding machine having a cylinder diameter of 20 mm and a mandrel diameter of 10 mm, and was extruded at a die temperature of 100° C. so as to be molded into a tube shape. After PTFE was ejected from an outlet of the die, the periphery of the die was covered by a heater, and the temperature around the outlet of the die was adjusted to 90° C. The molded tube was allowed to pass through a first drying furnace set at 150° C., a second drying furnace set at 220° C., and a sintering furnace set at 430° C. such that the tube was dried and sintered. The obtained tube had an inner diameter of 0.60 mm and a wall thickness of 0.028 mm. The surface of the obtained tube was coated with TetraEtch (registered trademark), washed with alcohol and water, and etched to prepare a PTFE tube according to an embodiment of the present invention. The obtained PTFE tube was cut to about 100 mm in length and used as a sample for tensile tests. A tensile test was performed under an atmosphere of 200° C. in accordance with the method described above. In addition, the obtained PTFE tube was cut to about 1000 mm and used as a sample for evaluation. On the other hand, a core wire having an outer diameter of 0.51 mm and a length of about 980 mm was prepared, and a heat stretching test was performed in accordance with the method described above. In addition, wetting tension was measured in accordance with the method described above.

Example 2

A preform prepared in the same manner as in Example 1 was introduced into an extrusion molding machine having a cylinder diameter of 30 mm and a mandrel diameter of 10 mm, and extruded at a die temperature of 90° C. so as to be molded into a tube shape. After PTFE was ejected from an outlet of the die, the periphery of the die was covered by a heater, and the temperature around the outlet of the die was adjusted to 80° C. In the same manner as in Example 1, the molded tube was allowed to pass through a drying furnace and a sintering furnace such that the tube was dried and sintered. The obtained tube had an inner diameter of 1.72 mm and a wall thickness of 0.038 mm. The surface of the obtained tube was coated with TetraEtch (registered trademark), washed with alcohol and water, and etched to prepare a PTFE tube according to an embodiment of the present invention. The obtained PTFE tube was cut to about 100 mm in length and used as a sample for tensile tests. A tensile test was performed under an atmosphere of 200° C. in accordance with the method described above. In addition, the obtained PTFE tube was cut to about 1000 mm and used as a sample for evaluation. On the other hand, a core wire having an outer diameter of 1.45 mm and a length of about 980 mm was prepared, and a heat stretching test was performed in accordance with the method described above. In addition, wetting tension was measured in accordance with the method described above.

Example 3

A preform prepared in the same manner as in Example 1 was introduced into an extrusion molding machine, and extruded at a die temperature of 100° C. so as to be molded into a tube shape. After PTFE was ejected from an outlet of the die, the periphery of the die was covered by a heater, and the temperature around the outlet of the die was adjusted to 80° C. In the same manner as in Example 1, the molded tube was allowed to pass through a drying furnace and a sintering furnace such that the tube was dried and sintered. The obtained tube had an inner diameter of 0.475 mm and a wall thickness of 0.028 mm. The surface of the obtained tube was allowed to pass through plasma, generated at an applied voltage of 10 kV and a frequency of 18 kHz using argon (Ar) as an excitation gas, at a speed of 6.0 m/min so as to be treated by plasma, whereby a PTFE tube according to an embodiment of the present invention was prepared. The obtained PTFE tube was cut to about 100 mm in length and used as a sample for tensile tests. A tensile test was performed under an atmosphere of 200° C. in accordance with the method described above. In addition, the obtained PTFE tube was cut to about 1000 mm and used as a sample for evaluation. On the other hand, a core wire having an outer diameter of 0.41 mm and a length of about 980 mm was prepared, and a heat stretching test was performed in accordance with the method described above. In addition, wetting tension was measured in accordance with the method described above.

Example 4

A preform prepared in the same manner as in Example 1 was introduced into an extrusion molding machine, and extruded at a die temperature of 100° C. so as to be molded into a tube shape. After PTFE was ejected from an outlet of the die, the periphery of the die was covered by a heater, and the temperature around the outlet of the die was adjusted to 100° C. In the same manner as in Example 1, the molded tube was allowed to pass through a drying furnace and a sintering furnace such that the tube was dried and sintered. The obtained tube had an inner diameter of 0.49 mm and a wall thickness of 0.038 mm. The surface of the obtained tube was coated with TetraEtch (registered trademark), washed with alcohol and water, and etched to prepare a PTFE tube according to an embodiment of the present invention. The obtained PTFE tube was cut to about 100 mm in length and used as a sample for tensile tests. A tensile test was performed under an atmosphere of 200° C. in accordance with the method described above. In addition, the obtained PTFE tube was cut to about 1000 mm and used as a sample for evaluation. On the other hand, a core wire having an outer diameter of 0.41 mm and a length of about 980 mm was prepared, and a heat stretching test was performed in accordance with the method described above. In addition, wetting tension was measured in accordance with the method described above.

Example 5

A preform prepared in the same manner as in Example 1 was introduced into an extrusion molding machine, and extruded at a die temperature of 80° C. so as to be molded into a tube shape. After PTFE was ejected from an outlet of the die, the periphery of the die was covered by a heater, and the temperature around the outlet of the die was adjusted to 60° C. In the same manner as in Example 1, the molded tube was allowed to pass through a drying furnace and a sintering furnace such that the tube was dried and sintered. The obtained tube had an inner diameter of 0.50 mm and a wall thickness of 0.022 mm. The surface of the obtained tube was allowed to pass through plasma, generated at an applied voltage of 10 kV and a frequency of 18 kHz using argon (Ar) as an excitation gas, at a speed of 2 m/min so as to be treated by plasma, whereby a PTFE tube according to an embodiment of the present invention was prepared. The obtained PTFE tube was cut to about 100 mm in length and used as a sample for tensile tests. A tensile test was performed under an atmosphere of 200° C. in accordance with the method described above. In addition, the obtained PTFE tube was cut to about 1000 mm and used as a sample for evaluation. On the other hand, a core wire having an outer diameter of 0.41 mm and a length of about 980 mm was prepared, and a heat stretching test was performed in accordance with the method described above. In addition, wetting tension was measured in accordance with the method described above.

Example 6

A preform prepared in the same manner as in Example 1 was introduced into an extrusion molding machine having a cylinder diameter of 44 mm, and extruded at a die temperature of 100° C. so as to be molded into a tube shape. After PTFE was ejected from an outlet of the die, the periphery of the die was covered by a heater, and the temperature around the outlet of the die was adjusted to 80° C. In the same manner as in Example 1, the molded tube was allowed to pass through a drying furnace and a sintering furnace such that the tube was dried and sintered. The obtained tube had an inner diameter of 2.68 mm and a wall thickness of 0.033 mm. The surface of the obtained tube was coated with TetraEtch (registered trademark), washed with alcohol and water, and etched to prepare a PTFE tube according to an embodiment of the present invention. The obtained PTFE tube was cut to about 100 mm in length and used as a sample for tensile tests. A tensile test was performed under an atmosphere of 200° C. in accordance with the method described above. In addition, the obtained PTFE tube was cut to about 1000 mm and used as a sample for evaluation. On the other hand, a core wire having an outer diameter of 2.42 mm and a length of about 980 mm was prepared, and a heat stretching test was performed in accordance with the method described above. In addition, wetting tension was measured in accordance with the method described above.

The results of each of the examples are shown in Table 1.

above, the variation in outer diameter when the core wire was covered with the PTFE tube (the coefficient of variation CV of the outer diameter) was small, and uniform elongation was observed. FIG. 2 shows a plot of the middle portion of Inequality (1) and the variation of outer diameter (the coefficient of variation CV of the outer diameter) for the PTFE tubes according to the examples, and it can be seen from this plot that Relational Inequality (1) is highly correlated with the uniform elongation when the core wire is covered with the PTFE tube.

Industrial Applicability

A PTFE tube according to the present invention is capable of being suitably used for tube liners, etc., and a multilayered tube using the PTFE tube according to the present invention is particularly suitable for medical tubes, etc.

Description of Reference Numeral

1 PTFE tube (section)

What is claimed is:

1. A polytetrafluoroethylene tube having a wall thickness of about 0.04 mm or less, wherein
   a coefficient of variation of an outer diameter of a core wire laminated with the polytetrafluoroethylene tube after a heat stretching test is 0.00180 or less, and

TABLE 1

| | | Example 1 | Example 2 | Example 3 | Example 4 | Example 5 | Example 6 |
|---|---|---|---|---|---|---|---|
| Inner diameter of tube | mm | 0.60 | 1.72 | 0.475 | 0.49 | 0.5 | 2.68 |
| Wall thickness of tube | mm | 0.028 | 0.038 | 0.028 | 0.038 | 0.022 | 0.033 |
| Tensile strain at break under atmosphere of 200° C. | % | 409.1 | 318.2 | 336.5 | 321.4 | 417.2 | 382.8 |
| tensile stress at 20% strain under atmosphere of 200° C. $\sigma_{20}$ | N/mm$^2$ | 7.56 | 10.89 | 7.56 | 8.55 | 5.76 | 7.80 |
| tensile stress at 50% strain under atmosphere of 200° C. $\sigma_{50}$ | N/mm$^2$ | 8.16 | 13.93 | 9.12 | 11.07 | 6.66 | 10.76 |
| Value of relational Inequality (1) of stress $\sigma_{20}$ and stress $\sigma_{50}$ ($0.1 \times \sigma_{20} + 0.3 \times \sigma_{50}$) | | 3.20 | 5.27 | 3.49 | 4.18 | 2.57 | 4.01 |
| Coefficient of variation of outer diameter CV | mm/mm | 0.00063 | 0.00180 | 0.00066 | 0.00114 | 0.00061 | 0.00112 |
| Wetting tension | mN/m | 70 or more | 70 or more | 46 | 60 | 70 or more | 62 |

It was confirmed from all of the examples that the tensile stress at 20% strain $\sigma_{20}$ (N/mm$^2$) of the polytetrafluoroethylene tube and the tensile stress at 50% strain $\sigma_{50}$ (N/mm$^2$) of the polytetrafluoroethylene tube satisfied Inequality (1)

the heat stretching test includes suspending a weight of 150 g per 0.1 mm$^2$ of a sectional area of the polytetrafluoroethylene tube and heating the polytetrafluoroethylene tube to 300° C. using a heater moving from top to bottom of the polytetrafluoroethylene tube at a speed of 100 mm/min, to stretch the polytetrafluoroethylene tube.

2. The polytetrafluoroethylene tube according to claim 1, wherein an inner diameter of the polytetrafluoroethylene tube is about 3.0 mm or less.

3. A medical tube using the polytetrafluoroethylene tube according to claim 1.

4. The polytetrafluoroethylene tube according to claim 1, wherein a wetting tension of either of or both outer and inner surfaces of the polytetrafluoroethylene tube is 46 mN/m or more.

5. The polytetrafluoroethylene tube according to claim 4, wherein an inner diameter of the polytetrafluoroethylene tube is about 3.0 mm or less.

6. A medical tube using the polytetrafluoroethylene tube according to claim 4.

\* \* \* \* \*